United States Patent [19]
Zdeb

[11] Patent Number: 5,232,448
[45] Date of Patent: Aug. 3, 1993

[54] PATIENT-CONTROLLED ANALGESIA DEVICE

[75] Inventor: Brian D. Zdeb, Round Lake Park, Ill.

[73] Assignee: Prime Medical Products, Round Lake Park, Ill.

[21] Appl. No.: 782,916

[22] Filed: Oct. 25, 1991

Related U.S. Application Data

[63] Continuation of Ser. No. 446,182, Dec. 5, 1989, abandoned.

[51] Int. Cl.$^5$ ................ A61M 1/00; A61M 31/00; A61M 5/178
[52] U.S. Cl. ............................ 604/153; 604/49; 604/51; 604/183; 604/185; 604/186; 604/246
[58] Field of Search ............... 604/153, 131–133, 604/151, 245–247, 36, 48, 51, 8, 9, 37, 93, 182, 185, 186, 212, 213, 246

[56] References Cited

U.S. PATENT DOCUMENTS

| | | | |
|---|---|---|---|
| 3,503,402 | 3/1970 | Schulte | 604/9 |
| 3,827,439 | 8/1974 | Schulte et al. | 604/185 |
| 4,121,584 | 10/1978 | Turner et al. | |
| 4,262,668 | 4/1981 | Schmidt | 604/246 |
| 4,544,371 | 10/1985 | Dormandy, Jr. et al. | |
| 4,548,607 | 10/1985 | Harris | |
| 4,560,375 | 12/1985 | Schulte et al. | 604/8 |
| 4,588,394 | 5/1986 | Schulte et al. | 604/9 |
| 4,596,558 | 6/1986 | Smith et al. | 604/246 |
| 4,601,707 | 7/1986 | Albisser et al. | 604/131 |
| 4,623,330 | 11/1986 | Laby et al. | |
| 4,627,839 | 12/1986 | Young | 604/131 |
| 4,634,427 | 1/1987 | Hannula et al. | 604/93 |
| 4,668,231 | 5/1987 | de Vries et al. | 604/153 |
| 4,699,615 | 10/1987 | Fischell et al. | 604/131 |
| 4,828,551 | 5/1989 | Gertler et al. | |
| 4,898,584 | 2/1990 | Borsanyi et al. | 604/153 |
| 4,898,585 | 2/1990 | Borsanyi et al. | 604/153 |

FOREIGN PATENT DOCUMENTS

PCT87/00758 2/1987 PCT Int'l Appl. .

OTHER PUBLICATIONS

Brochure "Infu-Med 400".
Primer "High-technology i.v. infusion devices," by Jane W. Kwan, *American Journal of Hospital Pharmacy*, vol. 46, Feb. 1989.
"A patient education program for a continuous infusion regimen on an outpatient basis," by Roos Nieweg, R.N., Janke Greidanus, M.D. and Elisabeth G. E. de Vries, M.D. *Career Nursing TM*, vol. 10(4), 1987.
Research "Evaluation of a disposable, nonelectronic, patient-controlled-analgesia device for postoperative pain" by Daniel P. Wermeling, Thomas S. Foster, Robert P. Rapp and Daniel E. Kenady, *Clinical Pharmacy*, vol. 6, Apr. 1987.
Research "Infusion phlebitis association with a programmble syringe-pump system versus gravity-feed minibottles," by Richard J. Baptista, David F. Driscoll, Janis A. Gallagher, Eva O'Keefe, Gregory J. Dumas, Scott M. Hammer and Philip P. Pacella, *Clinical Pharmacy*, vol. 6, Apr. 1987.
Clinical Note "Epidural administration of opiates by a new device", by F. Ingemar H. Ahlgren and Margareta B. E. Ahlgren, *Pain*, vol. 31 (1987).

*Primary Examiner*—C. Fred Rosenbaum
*Assistant Examiner*—Mark Bockelman
*Attorney, Agent, or Firm*—Leydig, Voit & Mayer

[57] ABSTRACT

An apparatus for the patient-controlled delivery of a beneficial agent comprising a dose reservoir for receiving and storing a beneficial agent, inlet means to and outlet means from the dose reservoir and pump means operative in response to an external force supplied to the pump means for drawing beneficial agent into the dose reservoir at a relatively constant rate and for discharging the beneficial agent out of the dose reservoir through the outlet means.

19 Claims, 3 Drawing Sheets

PATIENT-CONTROLLED ANALGESIA DEVICE

This is a continuation of copending application Ser. No. 446,182, file don Dec. 5, 1989 now abandoned.

TECHNICAL FIELD OF THE INVENTION

The present invention is directed to the controlled delivery of a pre-selected quantity of beneficial agent to a patient, and is more particularly directed to an apparatus and method for such delivery wherein the amount of beneficial agent administered can be controlled, up to a maximum preselected amount.

BACKGROUND OF THE INVENTION

Analgesics are often prescribed to relieve post-operative pain. The great difficulty in properly administering analgesics stems from a variety of factors. Age, hypatic function, renal function and other medication all affect the pharmacokinetics of analgesics and greatly affect the patient's need for analgesics. Thus while some patients never request (and thus do not need) analgesics for pain relief, some patients continue to suffer even after conventional doses of analgesics have been administered. Further, doctors tend to underprescribe the use of analgesics and nurses tend to underadminister them because of the fear that the patient will become addicted to the analgesic.

In the last several years, there has been considerable activity directed to devices and systems which permit the patient to control how much analgesic he or she receives up to a maximum predetermined limit. It has been found that as a group, patients controlling the quantity of analgesic they receive use less analgesic than patients who request the administration of an analgesic. Apparently, one factor is the psychological relief present when a patient knows he or she is in control of the amount of drug to be received, up to a maximum limit.

Devices that are on the market, or that are in the process of obtaining government regulatory approval, that are directed to the patient-controlled delivery of analgesics, include the Cardiff Palliator by Pye Dynamics Ltd. or Graseby Dynamics of the United Kingdom; the On-Demand Analgesic Computer (ODAC) Model JSI 0299 made by Janssen Scientific Instruments; a PCA infuser by Abbott Laboratories, Inc.; the Harvard PCA Pump by C. R. Bard Inc.; and a pump by Deltec Systems Inc. All of these pumps are large and bulky, the smallest pump being the Deltec pump, which is approximately as large as a telephone. All of the above-mentioned devices are electromechanical in nature, requiring a separate power source. Although the Deltec unit may conceivably be worn by patients, it is believed that the remainder of the pumps mentioned above confine the patient to a bed, or some other fixed location.

Another problem associated with these devices is that after the drug is loaded into the pump, certain control factors must be set by the nurse or other person who actually sets up the pump with the patient. Yet another problem with existing devices is that they are relatively expensive and may include some rather complex electronic components.

Another apparatus and system for patient-controlled analgesic is described in PCT International Publication Number 87/00758. The apparatus includes a dose reservoir for receiving and storing a dose of the analgesic, an inlet and an outlet to the dose reservoir, and control means operative by the patient for selectively expressing beneficial agent out of the dose reservoir through the outlet means. The inlet to the dose reservoir receives the analgesic under pressure from a pump means separate from the patient-controlled analgesic device itself which pumps the analgesic to the apparatus from an external supply source.

Known patient-controlled analgesic systems have several drawbacks. They are generally very complex and difficult to use. Often times they must be calibrated prior to use and this typically requires the user to be extensively trained in the use of the device. Also an auxiliary pumping source is typically needed to feed beneficial agent to the patient-controlled analgesic apparatus. In addition, such systems are comparatively expensive. Further, because of their size, many of the known patient-controlled analgesic systems are not suitable for ambulatory use. Thus there remains a need for an accurate, self-driven, low cost, patient-controlled analgesic apparatus, and in particular, such an apparatus that is adaptable for ambulatory use.

Accordingly it is a principal object of the present invention to provide a patient-controlled analgesic device which is self-driven. A related object is to provide such a device in which the device itself includes a single power source for both filling the device with beneficial agent and for discharging up to a maximum predetermined dose of the beneficial agent to the patient upon demand of the patient. It is a further related object to provide such a device wherein the power source has a linear fill rate over its entire fill range in order to prevent overdosing.

It is yet another object of the present invention to provide a patient-controlled analgesic device that can be used with prefilled containers of the beneficial agent to be administered to the patient. It is also an object of the invention to provide a patient-controlled analgesic device that is suitable for ambulatory use.

These and other objects and advantages of the present invention will become apparent from the following detailed description of the invention and from the accompanying drawings.

SUMMARY OF THE INVENTION

A patient-controlled analgesic device capable of delivering a full dose or intermittently a fractional dose of a beneficial agent such as, for example, an analgesic, an antibiotic, heparin, insulin, or the like is provided. The device includes a single power source comprising pump means which draws beneficial agent into the device at a relatively constant rate of flow and also serves as the means for delivering beneficial agent to the patient. To further control the rate at which beneficial agent is fed to the device, a restriction means (administration set) is used in combination with the patient-controlled analgesic device.

DETAILED DESCRIPTION OF THE PREFERRED EMBODIMENTS

Figure 1:
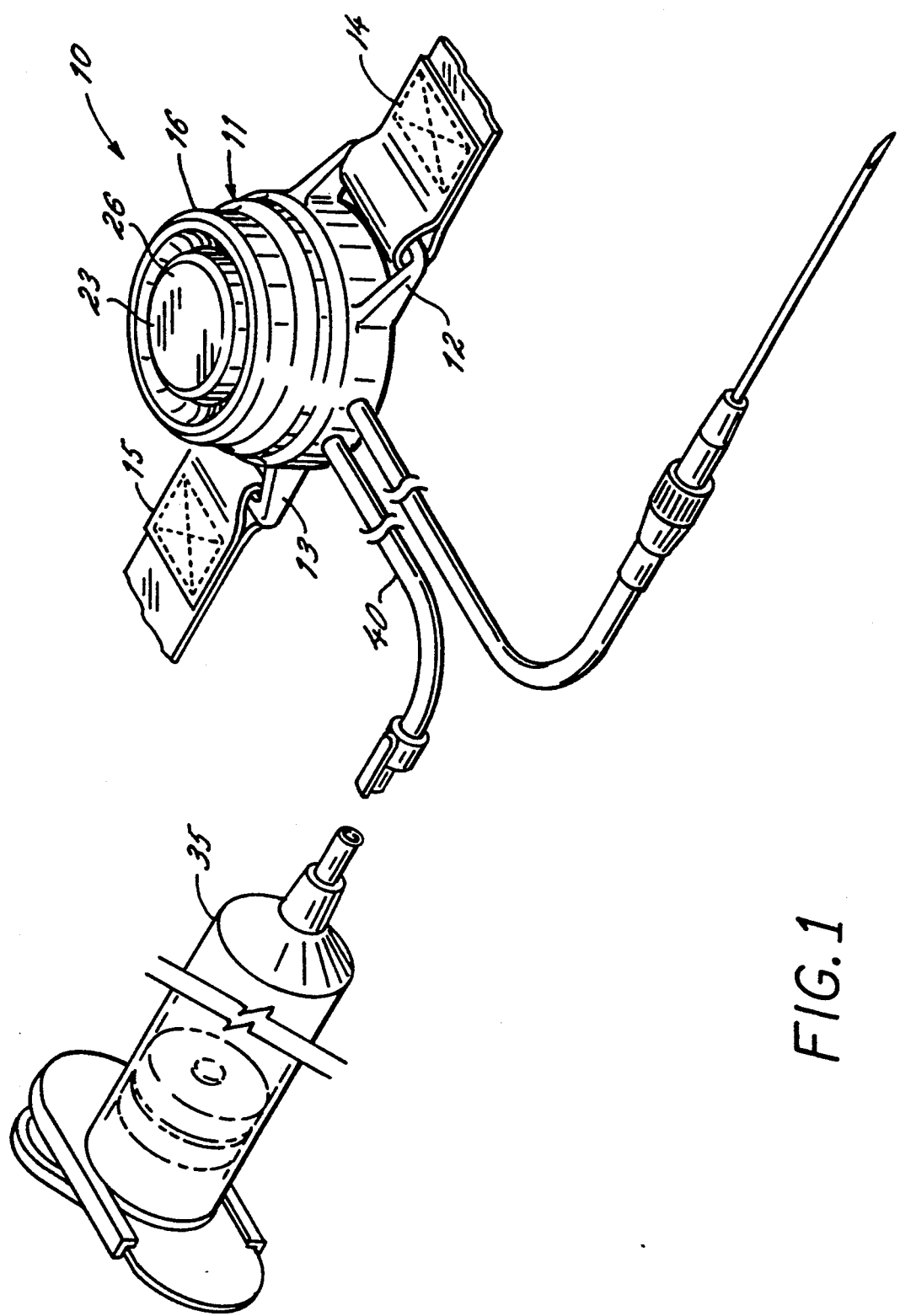
FIG. 1 is a perspective view of the patient-controlled analgesic device of the present invention and a supply source for beneficial agent.
Figure 2:
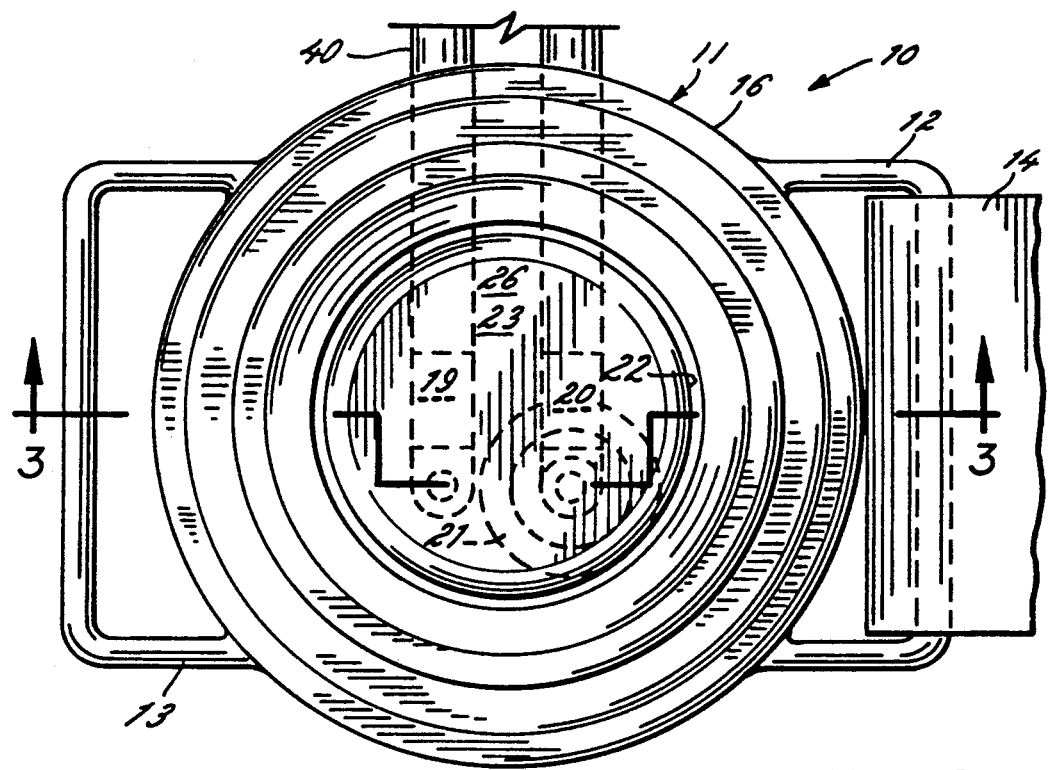
FIG. 2 is a top perspective view of the patient-controlled analgesic device and showing, in partial section the inlet and outlet means to the dose reservoir.
Figure 3:
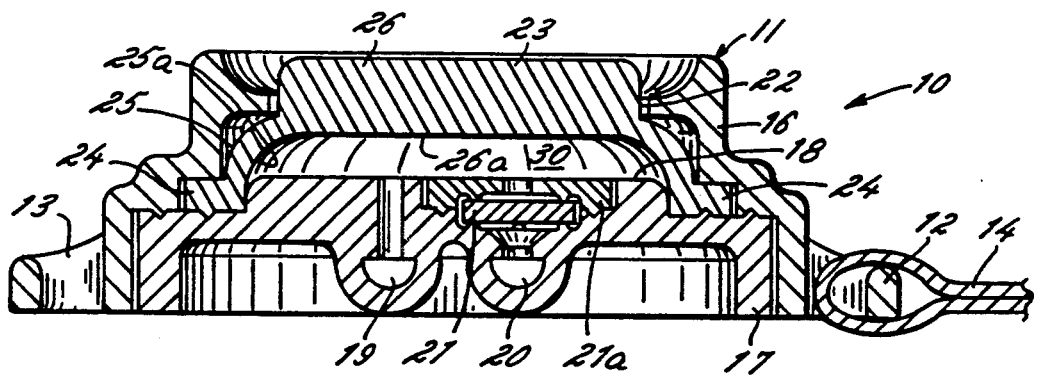
FIG. 3 is a cross-sectional view of the patient-controlled analgesic device taken along the line 3—3 in FIG. 2.

Referring now to FIGS. 1-3 the patient-controlled analgesic device 10 of the present invention includes a housing 11. Housing 11 forms mounting pins 12, 13 to which wrist band portions 14, 15 may be secured. The wrist band portions may be Velcro ® or other bands that are capable of mating and securing the device to a wrist. The device 10 may thus be worn in the same manner as a watch.

The housing 11 of the device 10 includes a casing 16 and a back plate 17 secured to the casing, as for example with a plurality of screws (not shown). A portion of the back plate 17 forms a raised plateau 18 that forms one wall of a dose reservoir 30. Back plate 17 further includes a dose reservoir inlet 19 in communication with the dose reservoir and a dose reservoir outlet 20 also in communication with the dose reservoir. Referring to FIG. 3, in the illustrated embodiment, the outlet 20 includes a disc valve 21, and valve seal 21a to sealingly engage disc valve 21 in communication with dose reservoir 30. Disc valve 21 is normally closed so that beneficial agent drawn into dose reservoir 30 is retained therein until expressed out of the device 10 by the patient, as will be more fully described below. It will be appreciated that the dose reservoir inlet 19 may include a valve means (not shown) or flow restrictive means (not shown) to limit backflow of beneficial agent through the inlet during operation of the device.

In the illustrated embodiment, pump means 23 has an annular cross section. Pump means 23 comprises a foot portion 24, an arcuate leg portion 25 and a head 26. The foot portion 24 of pump means 23 lies adjacent the plateau portion 18 of the back plate 17 and is in sealing engagement therewith. Arcuate-shaped leg portion 25 curves upwardly from foot portion 24 to head 26 of pump means 23. Head 26 of pump means 23 extends upwardly through annular opening 22 in casing 16 to facilitate access of the pump means to an external force, such as, for example, the patient. The interior portion 25a of arcuate-shaped leg portion 25 and the interior portion 26a of head 26 of pump means 23 together with the plateau 18 of back plate 17 define dose reservoir 30.

In accordance with one aspect of the present invention pump means 23 is designed so that it will draw beneficial liquid from a supply source 35, through conduit means 40 into dose reservoir 30 at a constant rate. It has been found that to accomplish that end, the arcuate-shaped portion 25 of pump means 23 should have a constant curvature over its entire length from foot portion 24 to head 26 and head 26 should be sufficiently rigid so that when pump means 23 is acted upon by an external force the arcuate-shaped leg portion 25 of pump means 23 will collapse under that force. The pump means so designed provides a substantially linear recovery rate throughout its entire range of motion relative to the dose reservoir. Stated another way, the rate at which the collapsed pump means recovers from a collapsed condition to its fully uncompressed starting position is linear over its entire stroke, from a fully compressed condition, as for example when the dose reservoir is completely emptied, to its original uncompressed condition, as for example when the dose reservoir is completely filled, and at all points between those two conditions.

The linear recovery rate of the pump means provides a constant suction to draw beneficial liquid from external supply source 35 into dose reservoir 30. Thus, after the pump means is depressed by an external force, such as the patient pushing on head 26 to discharge beneficial agent, upon release of the external force, head 26 returns to its original position at a controlled and linear rate. Accordingly, regardless of the position of the head relative to the dose reservoir after expressing beneficial agent from the dose reservoir by depressing the head, the incremental amount of beneficial agent drawn into the dose reservoir as the head rebounds to its original uncompressed position is directly proportional to the time the head was depressed by the external force. By way of example, if the recovery time to completely refill an emptied dose reservoir is T, then the recovery time will be one-half T for a dose reservoir that is only one-half emptied and one-fourth T for a dose reservoir that is only one-fourth emptied, et cetera.

The pump means is preferably constructed of a resilient material which is biocompatible with the human body and is likewise compatible with the beneficial agent to be administered to the patient. For example, silicone rubber is an acceptable resilient material. However, other elastomers can be used to construct the pump means.

In the illustrated embodiment of the invention shown in FIGS. 1-3, pump means 23 comprises a silicone rubber having a durometer of 30 to 50 (Shore A). A 30 to 50 durometer for the silicone elastomer pump means provides sufficient elasticity to perform the functions of both drawing beneficial agent from a supply source into the dose reservoir and expressing beneficial agent from the dose reservoir to the patient. It will be appreciated that a change in the durometer of the elastomer used for the pump means will affect the drawing power of the pump means and may thus affect the rate at which the dose reservoir is filled. For example, the greater the elastomer durometer, the greater the drawing power of the pump means will be.

As previously indicated, the head 26 of pump means 23 is more rigid than the arcuate-shaped leg portion 25. In the preferred embodiment, the pump means is a unitary structure so that head 26 must be thicker than the arcuate-shaped leg portion to impart the necessary rigidity to the head. Thus, head 26 must be sufficiently thick so that when external pressure is applied to it, pump means 23 is compressed by collapse of the arcuate-shaped leg portion 25. That is, the head 26 is sufficiently thick that it does not compress significantly under the externally-applied force. Further, as described, the arcuate-shaped leg portion 25 has a constant curvature over its entire length, and will collapse under the application of an external force in order to express beneficial agent out of the outlet means and to the patient.

In a preferred embodiment of the present invention, pump means 23 is formed from a silicone rubber elastomer with a durometer of 30 to 50 (Shore A), and the arcuate-shaped leg portion 25 has a thickness (in cross-section) of about two-thirds the thickness of head 26. It is especially preferred for such pump means that the head have a thickness of about 0.12 inch and the arcuate-shaped leg portion 25 have a width of about 0.08 inch. The arcuate-shaped leg portion 25 has a uniform radius of curvature over its entire length, and together with head 26 define a pump means 23 having an annular area of constant cross-section.

As depicted in FIGS. 1-3, the resilient compressible pump means 23 assumes a first uncompressed condition. In this condition the patient-controlled apparatus may be primed for subsequent use by the patient by filling the dose reservoir with liquid and removing air from the apparatus.

As previously indicated, pump means 23 is operable in response to the application of an external force applied to head 26 of pump means 23. The external force may be, for example, the finger or thumb of the patient pushing downwardly on head 26. In response to the external force applied to head 26 of pump means 23, the arcuate-shaped leg portion 25 collapses. As the arcuate-shaped leg portion 25 of pump means 23 collapses, the normally closed valve means 21 in outlet means 20 opens and beneficial agent is expressed from the dose reservoir, through the outlet means to the patient. The valve means 21 remains open as long as the external force is applied to the pump means. However, during that time the maximum amount of beneficial agent that will be expressed to the patient is a full dose. Upon release of the external force, the resilient pump means tends to rebound to its first uncompressed condition, valve means 21 returns to its normally closed position and the dose reservoir is sealed. Thus, as pump means 23 rebounds to its first uncompressed condition, at least a partial vacuum is created in the dose reservoir. The vacuum in the dose reservoir is sufficient to draw beneficial liquid from an external supply source 35 through conduit means 40 and into dose reservoir 30 to replenish beneficial agent that was expressed from the device. Because of the design of the pump means, it rebounds to its first uncompressed condition at a relatively constant rate and, therefore, liquid is likewise drawn from external supply source 35 into dose reservoir 30 at a relatively constant rate.

The dose reservoir 30 is filled in a predetermined time period which will depend on the volume of dose reservoir, the pump means employed and the restriction means, if any, between the beneficial agent supply source 35 and the device 10. It will be appreciated, however, that a patient-controlled analgesic device with a particular pumping rate and dose reservoir volume when manufactured may be used for a variety of dosage requirements by adjusting the concentration of beneficial agent in the supply source to be delivered to the device.

With the device as described, a patient who has depressed head 26 of pump means 23 and has thereby received a dose of beneficial agent may receive another full dose of beneficial agent after the expiration of predetermined refill time period T. While the patient may wait longer than the predetermined time period T if desired, the patient must wait at least the predetermined time period T in order to receive a full dose. However, if the patient depresses pump means 23 sometime before the predetermined time period T required to fill the dose reservoir has expired, the patient will receive only a fraction of the full dose. Because the rebound rate of the pump means is linear over the entire range of completely empty to completely filled, the dose fraction that the patient receives will be equal to the fraction of the refill time period T that has elapsed during the patient's intermittent demand for beneficial agent. For example, if the patient depresses the pump means at a time equal to one-half the predetermined fill time T, the patient will receive only one-half of a full dose volume. Thus no matter how often the patient depresses the pump means, he will never receive more than a single full dose of beneficial agent during the predetermined fill period T.

It will be appreciated that while pump mean 23 of the patient-controlled analgesic device 10 of the present invention is capable of drawing beneficial liquid into the dose reservoir 30 at a linear rate, the precise rate at which liquid is drawn may be controlled by suitably restricting the rate at which the beneficial liquid is drawn from the supply source. To that end, either the inlet means itself may be designed to limit its rate of flow, or some other restrictive means within the supply source or between the supply source and the inlet means may be used. In a preferred embodiment of the invention, a conventional administration set is used to control the rate at which beneficial agent is drawn from the supply source. Such administrative sets are available with flow restrictive orifices of a fixed or adjustable design and may be used advantageously in combination with the patient controlled analgesic device of the present invention to control the rate at which beneficial agent is delivered from the supply source.

Figure 4:
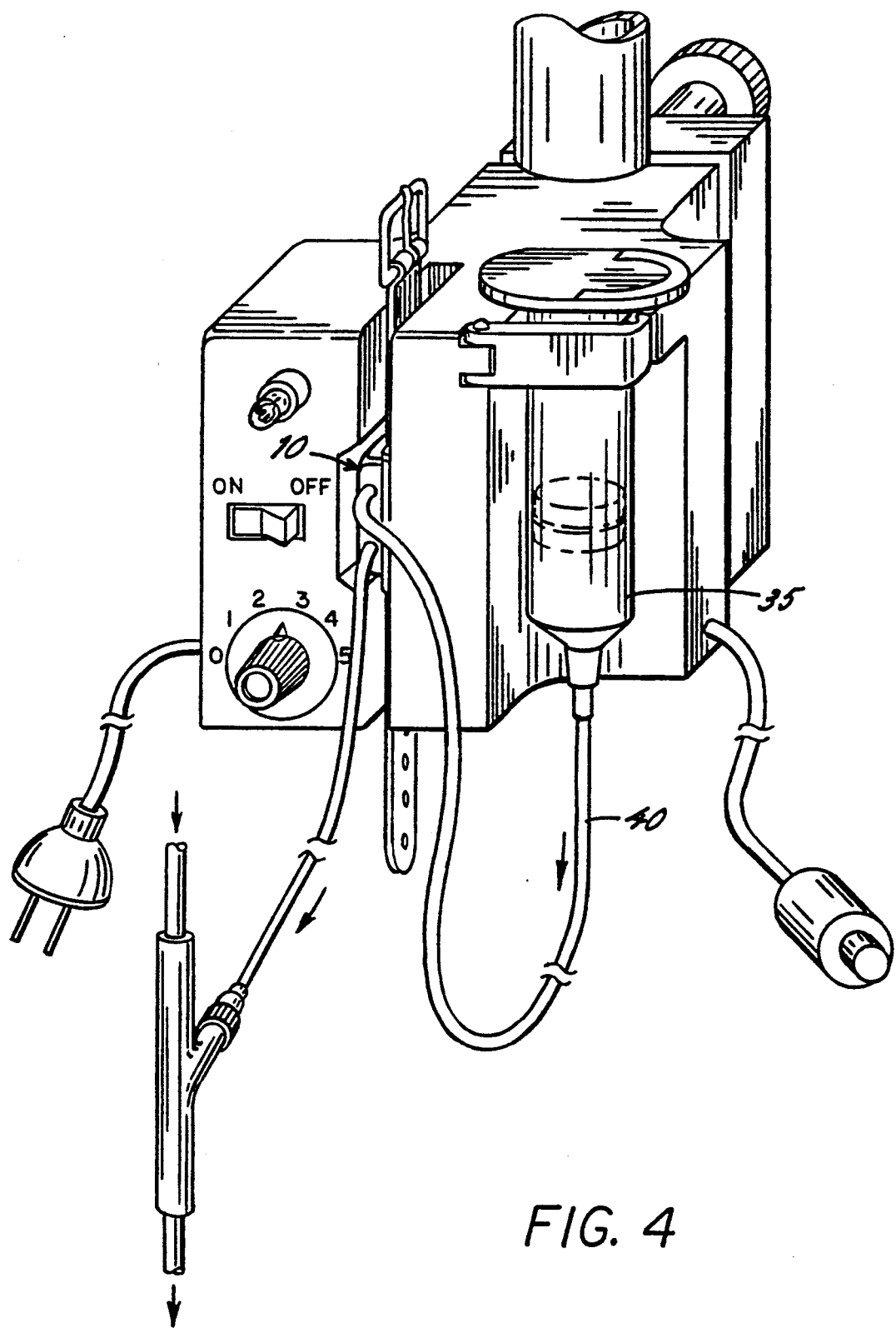
FIG. 4 is a perspective view of the patient-controlled analgesic device mounted in an electronic unit capable of administering beneficial agent to the patient at preselected time intervals.

As depicted in FIG. 4, the device 10 of the present invention may be used with automated equipment to deliver a dose of beneficial agent continuously or automatically at timed intervals, particularly when the patient is asleep. The automated equipment is capable of automatically depressing the pump means 23 of the device 10 at preset intervals and may be relatively inexpensive compared to a separate automated pump and power source. It need not be a sophisticated electronic pump because all metering and dosing of beneficial agent will still be done by the device 10, without an external pump. The automated equipment may carry a patient override to permit the patient to override the preset intervals for dose administration. Dosing with such an arrangement is still controlled by the device 10 itself, as previously described, so that patient overdosing is precluded.

The present invention thus provides an accurate, self-driven, low-cost patient controlled analgesic apparatus that is versatile in use. It can be used by ambulatory patients during their waking hours and it can be readily adapted for use by patients at night with relatively inexpensive automated equipment.

I claim as my invention:

1. An apparatus for patient-controlled delivery of a beneficial agent comprising
   (a) a dose reservoir for receiving and storing a dose of beneficial agent;
   (b) inlet means to said dose reservoir for receiving the beneficial agent from an external supply;
   (c) outlet means to said dose reservoir through which the beneficial agent in said dose reservoir exits said dose reservoir; and
   (d) pump means partially defining said dose reservoir operative in response to an external force supplied to said pump means for drawing beneficial agent into said dose reservoir at a relatively constant rate and for discharging the beneficial agent out of said dose reservoir through said outlet means, said pump means comprising an annular shaped arcuate wall means terminating at a foot, said arcuate wall means having a constant wall curvature and wall thickness extending from said foot to a centrally located head means, said head means having a rigidity substantially greater than the rigidity of the arcuate wall means to restrict the compression of said pumping means substantially to the said arcuate wall means, said pump means compressed in response to an external force applied to said pump means so as to advance the beneficial agent from said dose reservoir to said outlet means, and upon removal of the external force the pump means returns to the uncompressed condition at relatively constant rate, wherein upon retuning to the uncompressed condition the pressure in said dose reservoir is lower ralative to the pressure in the external supply so that beneficial agent is drawn into said dose reservoir from the external supply via suction at a relatively constant rate.

2. The apparatus of claim 1, wherein said pump means may be actuated by the patient.

3. The apparatus of claim 2, wherein the resilient material of said pump means prevents delivery of a dose quantity of the beneficial agent to the patient in excess of the dose quantity within a preselected time period by returning to the uncompressed condition at a relatively constant rate.

4. The apparatus of claim 1, wherein said pump means and said dose reservoir permit the delivery of no greater than a dose quantity of beneficial agent to be delivered to the patient within a preselected time period.

5. The apparatus of claim 1, including downstream conduit secured at one end to said outlet means and having a distal end adaptable for securement to an intravenous catheter.

6. The apparatus in accordance with claim 1, wherein said apparatus is free of any electrical power source.

7. The apparatus in accordance with claim 1, further comprising means for automatically compressing the pump means at preset intervals, wherein said pump means is actuated at timed intervals by the automatic compressing means.

8. The apparatus in accordance with claim 1, wherein said pump means may be repeatedly actuated by the patient, said pump means permitting delivery of fractional doses of the beneficial agent to the patient of a delivery rate controlled by said pump means so as to prevent exceeding a pre-determined dosage within a pre-determined period of time.

9. The apparatus in accordance with claim 1, comprising a housing in conjunction with the said pumping means defining said dose reservoir.

10. The apparatus in accordance with claim 1, including, in combination, an upstream conduit in communication with said inlet means to said dose reservoir, said upstream conduit comprising means for controlling the rate of flow of beneficial agent to said dose reservoir in response to actuation of said pump means.

11. The apparatus of claim 10, wherein said pump means may be repeatedly actuated by the patient at times less than required for a full dose, said pump means permitting the delivery of fractional doses of the beneficial agent to the patient from said dose reservoir.

12. The apparatus of claim 11, wherein said pump means prevents delivery of a quantity of beneficial agent to the patient in excess of a dose quantity within a preselected time period.

13. The apparatus of claim 10, wherein said pump means and said dose reservoir permit the delivery of no greater than a dose quantity of beneficial agent to be delivered to the patient within a preselected time period.

14. The apparatus of claim 10, including downstream conduit secured at one end to said outlet and having a distal end adaptable for securement to an intravenous catheter.

15. The apparatus in accordance with claim 10, wherein said apparatus is free of any electrical power source.

16. The apparatus in accordance with claim 10, said apparatus further comprising:
means for automatically compressing the pump means at preset intervals, wherein said pump means is actuated at timed intervals, wherein said pump means is actuated at timed intervals by said automatic compressing means.

17. The apparatus in accordance with claim 10, wherein said pump means may be repeatedly actuated by the patient, said pump means permitting the delivery of multiple doses of the beneficial agent to the patient at a controlled delivery rate.

18. The apparatus in accordance with claim 10, comprising a housing in conjunction with the said pumping means defining said dose reservoir.

19. A patient-controlled method of injecting a beneficial agent into a patient, said method comprising:
(a) compressing by means of an external force a collapsible dose reservoir filled with a beneficial agent so as to expel the agent therefrom via outlet means into a conduit leading to the patient, said collapsible dose reservoir capable of receiving and storing a dose of the beneficial agent and comprising inlet means to the dose reservoir for receiving the beneficial agent from an external supply, outlet means to the dose reservoir through which the beneficial agent in the dose reservoir exits the dose reservoir, and pump means operative in response to an external force supplied to said pump means for drawing beneficial agent into said dose reservoir at a relatively constant rate and for discharging the beneficial agent out of said dose reservoir through said outlet means, said pump means comprising an annular shaped arcuate wall means terminating at a foot, said arcuate wall means having a constant wall curvature and wall thickness extending from the said foot to a centrally located head means, said head means having a rigidity substantially greater than the rigidity of the arcuate wall means to restrict the compression of said pump means substantially to the said arcuate wall means, said pump means compressed in response to an external force applied to said pump means so as to advance the beneficial agent from said dose reservoir to said outlet means, and upon removal of the external force the pump means returns to the uncompressed condition at a relatively constant rate, wherein upon returning to the uncompressed condition the pressure in said dose reservoir is lower relative to the pressure in the external supply so that beneficial agent is drawn into sad dose reservoir from the external supply via suction at a relatively constant rate; and
(b) removing the external force so as to enable the dose reservoir to refill with the beneficial agent at a relatively constant rate by drawing the beneficial agent into the dose reservoir from the external supply via suction.

* * * * *